United States Patent [19]

Suresh et al.

[11] Patent Number: 5,840,648
[45] Date of Patent: Nov. 24, 1998

[54] CATALYST FOR THE MANUFACTURE OF ACRYLONITRILE AND HYDROGEN CYANIDE

[75] Inventors: Dev Dhanaraj Suresh, Hudson; Christos Paparizos, Willowick; Michael J. Seely, Twinsburg; Maria Strada Friedrich, Lyndhurst; Tama Lee Drenski, Twinsburg, all of Ohio

[73] Assignee: The Standard Oil Company, Cleveland, Ohio

[21] Appl. No.: 923,878

[22] Filed: Sep. 2, 1997

[51] Int. Cl.⁶ .............. B01J 23/00; B01J 23/18; B01J 23/04
[52] U.S. Cl. .......... 502/306; 502/307; 502/303; 502/302; 502/300; 502/305
[58] Field of Search .................... 502/300, 302, 502/303, 305, 306, 307, 308, 310, 311, 312, 313, 314, 315, 316, 317, 319, 320, 321, 322, 323, 324, 325, 328, 329, 330, 332, 335, 336, 337, 338, 340, 341, 342, 343, 344, 349, 352, 353, 354, 355

[56] References Cited

U.S. PATENT DOCUMENTS

| | | |
|---|---|---|
| 4,040,978 | 8/1977 | Li . |
| 4,168,246 | 9/1979 | Li . |
| 4,186,152 | 1/1980 | Yamamoto et al. . |
| 4,190,608 | 2/1980 | Grasselli et al. . |
| 4,278,614 | 7/1981 | Umemura et al. . |
| 4,290,922 | 9/1981 | Umemura et al. . |
| 4,374,759 | 2/1983 | Khoobiar ........................ 502/249 |
| 4,377,534 | 3/1983 | Grasselli et al. . |
| 4,388,223 | 6/1983 | Ferlazzo et al. . |
| 4,405,498 | 9/1983 | Ebner et al. . |
| 4,410,450 | 10/1983 | Sasaki et al. . |
| 4,415,482 | 11/1983 | Ebner . |
| 4,565,658 | 1/1986 | Ebner . |
| 4,732,884 | 3/1988 | Sarumaru et al. . |
| 4,766,232 | 8/1988 | Grasselli et al. . |
| 4,814,479 | 3/1989 | Engelbach et al. . |
| 4,863,891 | 9/1989 | Grasselli et al. . |
| 4,946,819 | 8/1990 | Sasaki et al. . |
| 4,981,830 | 1/1991 | Sasaki et al. . |
| 5,059,573 | 10/1991 | Sasaki et al. . |
| 5,071,814 | 12/1991 | Sasaki et al. . |
| 5,093,299 | 3/1992 | Suresh et al. . |
| 5,094,990 | 3/1992 | Sasaki et al. . |
| 5,132,269 | 7/1992 | Sasaki et al. . |
| 5,134,105 | 7/1992 | Paparizos et al. ........................ 502/205 |
| 5,138,100 | 8/1992 | Matsuura . |
| 5,139,988 | 8/1992 | Sasaki et al. . |
| 5,144,090 | 9/1992 | Honda et al. . |
| 5,166,119 | 11/1992 | Oh-Kita et al. . |
| 5,177,048 | 1/1993 | Chen et al. . |
| 5,215,952 | 6/1993 | Bielmeier et al. . |
| 5,218,146 | 6/1993 | Takata et al. ........................ 562/535 |
| 5,223,469 | 6/1993 | Chen et al. . |
| 5,235,088 | 8/1993 | Paparizos et al. ........................ 558/324 |
| 5,245,083 | 9/1993 | Matsuura . |
| 5,364,825 | 11/1994 | Neumann et al. . |
| 5,543,532 | 8/1996 | Kourtakis . |
| 5,556,984 | 9/1996 | Blanchard et al. . |
| 5,583,086 | 12/1996 | Tenten et al. . |
| 5,602,280 | 2/1997 | Nagai et al. ........................ 562/546 |

FOREIGN PATENT DOCUMENTS

| | | |
|---|---|---|
| 1031662 A | 3/1989 | China . |
| 1033014 A | 5/1989 | China . |
| 32012-A | 7/1981 | European Pat. Off. . |
| 750942-A2 | 1/1997 | European Pat. Off. . |
| 767164-A1 | 4/1997 | European Pat. Off. . |
| 204407-A | 11/1983 | Germany . |
| 57019037-A | 2/1982 | Japan . |
| 57081838-A | 5/1982 | Japan . |
| 58040149-A | 3/1983 | Japan . |
| 58046055-A | 3/1983 | Japan . |
| 08027089-A | 7/1984 | Japan . |
| 59204163-A | 11/1984 | Japan . |
| 60122041-A | 6/1985 | Japan . |
| 2059-046-A | 8/1988 | Japan . |
| 06199767-A | 12/1992 | Japan . |
| 06199768-A | 1/1993 | Japan . |
| 07215925-A | 12/1993 | Japan . |
| 07303836-A | 5/1994 | Japan . |
| 08027088-A | 7/1994 | Japan . |
| 08141401-A | 11/1994 | Japan . |
| 08266899-A | 3/1995 | Japan . |
| 09040628-A | 7/1995 | Japan . |
| 9414759-A1 | 7/1994 | WIPO . |
| 9505241-A1 | 2/1995 | WIPO . |
| 9508391-A1 | 3/1995 | WIPO . |
| 9623766-A1 | 8/1996 | WIPO . |
| 96266899 | 10/1996 | WIPO . |

*Primary Examiner*—Elizabeth D Wood
*Attorney, Agent, or Firm*—Michael F. Esposito; David J. Untener

[57] ABSTRACT

A catalyst composition comprising a complex of catalytic oxides of iron, bismuth, molybdenum and calcium and characterized by the following empirical formula:

$$A_a B_b C_c D_d Fe_e Bi_f Mo_{12} O_x$$

where A=one or more of Li, Na, K, Rb and Cs or mixtures thereof

B=one or more of Mg, Mn, Ni, Co, Ag, Pb, Re, Cd and Zn or mixtures thereof

C=one or more of Ce, Cr, Al, Sb, P, Ge, La, Sn, V and W or mixtures thereof

D=one or more of Ca, Sr, Ba or mixtures thereof and a=0.01 to 1.0; b and e=1.0–10; c, d, and f=0.1 to 5.0 and x is a number determined by the valence requirements of the other elements present.

18 Claims, No Drawings

CATALYST FOR THE MANUFACTURE OF ACRYLONITRILE AND HYDROGEN CYANIDE

BACKGROUND OF THE INVENTION

FIELD OF THE INVENTION

The present invention relates to an improved catalyst for use in the ammoxidation of unsaturated hydrocarbon to the corresponding unsaturated nitrile which unexpectedly provides increased yields in coproduct HCN without significant decrease in the yield of the unsaturated nitrile. In particular, the present invention is directed to an improved process and catalyst for the ammoxidation of propylene and/or isobutylene to acrylonitrile and/or methacrylonitrile, respectively, with an attendant increase in production of hydrogen cyanide coproduct without significant decrease in nitrile yield.

There are many patents related to the production of acrylonitrile by the use of bismuth-molybdenum-iron fluidized bed catalysts. In particular, Great Britain Patent 1436475; U.S. Pat. Nos. 4,766,232; 4,377,534; 4,040,978; 4,168,246; 5,223,469 and 4,863,891 are each directed to bismuth-molybdenum-iron catalysts which may be promoted with the Group II elements to produce acrylonitrile. In addition, U.S. Pat. No. 4,190,608 discloses similarly promoted bismuth-molybdenum-iron catalyst for oxidation of olefins. Finally, recently issued U.S. Pat. No. 5,093,299 is directed to bismuth-molybdenum promoted catalysts which show high yields of acrylonitrile. Catalysts containing oxides of iron, bismuth and molybdenum, promoted with suitable elements, as described in the aforementioned patents have long been used for the conversion of propylene at elevated temperatures in the presence of ammonia and oxygen (usually in the form of air) to manufacture acrylonitrile. Acrylonitrile has been attained as a major product while hydrogen cyanide has been maintained as the major coproduct.

In the ammoxidation of propylene or isobutylene to its corresponding unsaturated nitrile, acrylonitrile-methacrylonitrile, respectively, it has long been the goal of researchers to maximize the acrylonitrile or methacrylonitrile production. However, recently the main coproduct of this ammoxidation reaction, hydrogen cyanide, has taken on an increasingly important economic consideration. In fact, in certain operations, the maximization of coproduct yields for hydrogen cyanide will be highly desirable especially if this increase in yield of hydrogen cyanide were achieved without the normal attendant loss in acrylonitrile production levels.

The operating conditions in an acrylonitrile reactor can be changed to increase the yield of hydrogen cyanide. However, changing of the operating conditions to increase the yield of hydrogen cyanide has always led to an economically unacceptable decrease in the production yields of acrylonitrile. Typically, for every one percent of hydrogen cyanide production increase, a decrease in two percent of acrylonitrile is seen. The present invention is directed to a solution to this problem.

SUMMARY OF THE INVENTION

It is the primary object of the present invention to obtain a novel ammoxidation catalyst which increases the yields of hydrogen cyanide coproduct produced during the manufacture of acrylonitrile while maintaining the acrylonitrile production levels at substantially the same levels.

It is a further object of the present invention to obtain a novel ammoxidation catalyst that at comparable operating conditions increases the yield of hydrogen cyanide without economically unacceptable losses in acrylonitrile production.

Additional objects and advantages of the invention will be set forth in part in the description which follows and in part will be obvious from the description or may be learned by the practice of the invention. The objects and advantages of the invention may be realized and attained by means of the instrumentalities and combinations particularly pointed in the appended claims.

To achieve the foregoing objects and in accordance with the purposes of the invention as embodied and appropriately described herein the catalyst of the present invention is characterized by the following empirical formula:

$$A_a B_b C_c D_d Fe_e Bi_f Mo_{12} O_x$$

where A=one or more of Li, Na, K, Rb and Cs or mixtures thereof
  B=one or more of Mg, Mn, Ni, Co, Ag, Pb, Re, Cd and Zn or mixtures thereof
  C=one or more of Ce, Cr, Al, Sb, P, Ge, La Sn, V and W or mixtures thereof
  D=one or more of Ca, Sr, Ba or mixtures thereof
and a=0.01 to 1.0; b and e=1.0–10; c, d, and f=0.1 to 5.0 and x is a number determined by the valence requirements of the other elements present.

In the preferred embodiment of the present invention, A is selected to be one or more of lithium, sodium, potassium and cesium, especially preferred being cesium and potassium.

In another preferred embodiment, B is selected from the group consisting of magnesium, manganese, nickel and cobalt, or mixtures thereof.

In still another preferred embodiment, C is selected from the group comprising cerium, chromium, antimony, phosphorus, germanium, tungsten, or mixtures thereof, especially preferred being cerium, chromium, phosphorus, and germanium.

In a further preferred embodiment of the present invention, D is selected from the group consisting of Ca, Sr and mixtures thereof, especially preferred being Ca.

In still another preferred embodiment of the present invention, a may range from about 0.05 to 0.9, especially preferred being above 0.1 to 0.7.

In a further preferred embodiment of the present invention, b and e may range from about 2 to 9, especially preferred being 2 to 8. In still a further preferred embodiment of the present invention, c, d and f may range from about 0.1 to 4, especially preferred being 0.1 to 3.

The catalyst of the present invention can be used either supported or unsupported. Preferably the catalyst is supported on silica, alumina or zirconium or mixtures thereof, especially preferred being silica.

The catalysts of the present invention may be prepared by any of the numerous methods of catalyst preparation which are known to those of skill in the art. For example, the catalyst may be manufactured by co-precipitating the various ingredients. The co-precipitating mass may then be dried and ground to an appropriate size. Alternatively, the co-precipitated material may be slurried and spray dried in accordance with conventional techniques. The catalyst may be extruded as pellets or formed into spheres in oil as is well known in the art. Alternatively, the catalyst components may be mixed with a support in the form of the slurry followed by drying or they may be impregnated on silica or other supports. For particular procedures for manufacturing the catalyst, see U.S. Pat. Nos. 5,093,299; 4,863,891 and 4,766, 232 assigned to the Assignee of the present invention, herein incorporated by reference.

Typically, the A component of the catalyst may be introduced into the catalyst as an oxide or as a salt which upon calcination will yield the oxide. Preferably, salts such as nitrates which are readily available and easily soluble are used as the means of incorporating the A element into the catalyst.

Bismuth may be introduced into the catalyst as an oxide or as a salt which upon calcination will yield the oxide. The water soluble salts which are easily dispersed but form stable oxides upon heat treating are preferred. An especially preferred source for introducing bismuth is bismuth nitrate which has been dissolved in a solution of nitric acid.

To introduce the iron component into the catalyst, one may use any compound of iron which, upon calcination will result in the oxides. As with the other elements, water soluble salts are preferred for the ease with which they may be uniformly dispersed within the catalyst. Most preferred is ferric nitrate.

Cobalt, nickel and magnesium may also be introduced into the catalyst using nitrate salts. However, magnesium may also be introduced into the catalyst as an insoluble carbonate or hydroxide which upon heat treating results in an oxide.

The molybdenum component of the catalyst may be introduced from any molybdenum oxide such as dioxide, trioxide, pentoxide or heptaoxide. However, it is preferred that a hydrolizable or decomposable molybdenum salt be utilized as the source of the molybdenum. The most preferred starting material is ammonium heptamolybdate.

Phosphorus may be introduced in the catalyst as an alkaline metal salt or alkaline earth metal salt or the ammonium salt but is preferably introduced as phosphoric acid. Calcium which is an essential ingredient in the catalyst of the present invention can be added via pre-formation of calcium molybdate or by impregnation or by other means known in the art. (Usually added as Ca-nitrate, along with the other nitrates.)

DETAILED DESCRIPTION OF THE INVENTION

The present invention is directed to an ammoxidation catalyst characterized by the following empirical formula:

$$A_a B_b C_c D_d Fe_e Bi_f MO_{12} O_x$$

where A=one or more of Li, Na, K, Rb and Cs or mixtures thereof

B=one or more of Mg, Mn, Ni, Co, Ag, Pb, Re, Cd and Zn or mixtures thereof

C=one or more of Ce, Cr, Al, Sb, P, Ge, La Sn, V and W or mixtures thereof

D=one or more of Ca, Sr, Ba or mixtures thereof and a=0.01 to 1.0; b and e=1.0–10; c, d, and f=0.1 to 5.0 and x is a number determined by the valence requirements of the other elements present.

The catalysts are prepared by mixing an aqueous solution of ammonium heptamolybdate with a silica sol to which a slurry containing the compounds, preferably nitrates of the other elements, is added. The solid material is then dried, denitrified and calcined. Preferably the catalyst is spray-dried at a temperature of between 110° C. to 350° C., preferably 110° C. to 250° C., most preferably 110° C. to 180° C. The denitrification temperature may range from 100° C. to 450° C., preferably 150° C. to 425° C. Finally, calcination takes place at a temperature of between 300° C. to 700° C., preferably between 350° C. to 650° C.

The following Examples are set forth below for illustrative purposes only.

TABLE I

| Examples | Catalyst Composition | Conv | AN | HCN |
|---|---|---|---|---|
| I. Effect of Operating Conditions on HCN Yield and AN Yield | | | | |
| 1 Comparative | $Cs_{0.1}K_{0.1}Ni_{7.6}Mg_{3.1}Fe_4Bi_{0.5}Ce_{0.5}Cr_{0.5}Mo_{15.6}O_x$ | 98.0 | 75.5 | 8.1 |
| 2 Comparative | Incr. pressure from 9.5 to 18.0 psig | 96.9 | 69.1 | 9.0 |
| 3 Comparative | Raise $NH_3/C_3^=$ from 1.2 to 1.3 | 95.3 | 67.7 | 9.3 |
| II. Comparative Examples | | | | |
| 4 | $Cs_{0.1}K_{0.1}Ni_{6.2}Mg_{2.5}Fe_2Bi_{0.5}Ce_{0.5}W_{2.3}Mo_{10}O_x$ | 94.0 | 67.1 | 8.1 |
| 5 | $K_{0.1}Ni_{2.5}Co_{4.5}Fe_3Bi_1P_{0.5}Mo_{12}O_x$ | 97.3 | 71.3 | 7.9 |
| 6 | $Cs_{0.1}K_{0.1}Ni_{6.2}Mg_{2.5}Fe_2Bi_{0.5}Ce_{0.5}P_1Mo_{10.8}O_x$ | 95.7 | 64.4 | 7.7 |
| III. Examples of Invention | | | | |
| 7 | $Cs_{0.1}K_{0.1}Ni_{6.2}Mg_{2.5}Fe_2Bi_{0.5}Ce_{0.5}Ca_{0.5}Mo_{12.8}O_x$ | 97.7 | 73.4 | 8.2 |
| 8 | $Cs_{0.1}K_{0.1}Ni_{6.2}Mg_{2.5}Fe_2Bi_{0.5}Ce_{0.5}Ca_{1.0}Mo_{13.4}O_x$ | 98.4 | 72.3 | 8.8 |
| 9 | $Cs_{0.1}K_{0.1}Ni_{6.2}Mg_{2.5}Fe_2Bi_{0.5}Ce_{0.5}Ca_{1.25}Mo_{13.6}O_x$ | 98.2 | 70.9 | 9.4 |
| 10 | $Cs_{0.1}K_{0.1}Ni_{6.2}Mg_{2.5}Fe_2Bi_{0.5}Ce_{0.5}Ca_{1.5}Mo_{13.85}O_x$ | 98.0 | 74.2 | 8.6 |
| 11 | $Cs_{0.1}K_{0.1}Ni_{6.2}Mg_{2.5}Fe_4Bi_{0.5}Ce_{0.5}Ca_{0.75}Mo_{15.55}O_x$ | 98.2 | 74.9 | 8.3 |
| 12 | Raise $NH_3/C_3^=$ to 1.25 and $Air/C_3^=$ to 10.1 | 98.2 | 74.5 | 9.2 |

Comparative Examples 1 to 6 and Examples 7 to 12 were tested under substantially the same conditions in a 40 cc fluid bed reactor at a throughput of between 0.10 to 0.12 wwh using a feed containing a mixture of 1 $C_3^=/1.2$ $NH_3/$ 9.8–10 Air at 430° C. to 460° C. and a psig of 15.

While the present invention has been described in conjunction with the specific embodiment set forth above, it is evident that many alternatives, modifications, and variations will be apparent to those skilled in the art in light of the foregoing description. Accordingly, it is intended to embrace all such alternatives, modifications and variations as fall within the spirit and broad scope of the appended claims.

What is claimed is:

1. A catalyst composition comprising a complex of catalytic oxides of iron, bismuth, molybdenum and calcium and characterized by the following empirical formula:

$$A_a B_b C_c D_d Fe_e Bi_f Mo_{12} O_x$$

where

A=one or more of Li, Na, K, Rb and Cs or mixtures thereof

B=one or more of Mg, Mn, Ni, Co, Ag, Pb, Re, Cd and Zn or mixtures thereof

C=one or more of Ce, Cr, Al, Sb, P, Ge, La, Sn, V and W or mixtures thereof

D=one or more of Ca, Sr, Ba or mixtures thereof and a=0.01 to 1.0; b and e=1.0–10; c, d, and f=0.1 to 5.0 and x is a number determined by the valence requirements of the other elements present.

2. The catalyst of claim 1 supported on an inert support selected from the group consisting of silica, alumina zirconia, and mixtures thereof.

3. The catalyst of claim 1 wherein A is selected from the group consisting of cesium, potassium or mixtures thereof.

4. The catalyst of claim 3 where A is a mixture of cesium and potassium.

5. The catalyst of claim 1 wherein B is one or more of Mg, Mn, Ni, Co and mixtures thereof.

6. The catalyst of claim 5 wherein B is one or more of Mg, Ni, Co and mixtures thereof.

7. The catalyst of claim 1 wherein C is one or more of Ce, Cr, Sb, P, Ge, W and mixtures thereof.

8. The catalyst of claim 7 wherein C is one or more of Ce, Cr, P, Ge and mixtures thereof.

9. The catalyst of claim 1 wherein D is one or more of Ca, Sr and mixtures thereof.

10. The catalyst of claim 1 wherein D is selected to be Ca.

11. The catalyst of claim 1 wherein a ranges from 0.05 to 0.9.

12. The catalyst of claim 11 wherein a ranges from about 0.1 to 0.7.

13. The catalyst of claim 1 wherein b and e range from about 2 to 9.

14. The catalyst of claim 13 wherein b and e range from 2 to 8.

15. The catalyst of claim 1 wherein c, d and f range from about 0.1 to 4.

16. The catalyst of claim 15 wherein c, d and f range from 0.1 to 3.

17. The catalyst of claim 9 wherein d ranges from 0.1 to 4.

18. The catalyst of claim 17 wherein d ranges from 0.1 to 3.

* * * * *